(12) United States Patent
He et al.

(10) Patent No.: US 10,317,365 B2
(45) Date of Patent: Jun. 11, 2019

(54) CORONA DISCHARGE ASSEMBLY, ION MOBILITY SPECTROMETER AND CORONA DISCHARGE METHOD

(71) Applicant: Nuctech Company Limited, Beijing (CN)

(72) Inventors: Wen He, Beijing (CN); Hua Peng, Beijing (CN); Yangtian Zhang, Beijing (CN); Yuntai Bao, Beijing (CN); Changzhuo Chen, Beijing (CN); Haichao Zhou, Beijing (CN)

(73) Assignee: Nuctech Company Limited, Beijing (CN)

( * ) Notice: Subject to any disclaimer, the term of this patent is extended or adjusted under 35 U.S.C. 154(b) by 0 days.

(21) Appl. No.: 15/578,536

(22) PCT Filed: Aug. 9, 2016

(86) PCT No.: PCT/CN2016/094164
§ 371 (c)(1),
(2) Date: Nov. 30, 2017

(87) PCT Pub. No.: WO2017/113804
PCT Pub. Date: Jul. 6, 2017

(65) Prior Publication Data
US 2018/0292353 A1    Oct. 11, 2018

(30) Foreign Application Priority Data

Dec. 31, 2015   (CN) .......................... 2015 1 1032539

(51) Int. Cl.
*G01N 27/68*  (2006.01)
*G01N 27/62*  (2006.01)
(Continued)

(52) U.S. Cl.
CPC ........... *G01N 27/68* (2013.01); *G01N 27/622* (2013.01); *H01J 49/061* (2013.01); *H01J 49/18* (2013.01)

(58) Field of Classification Search
CPC ..... G01N 27/68; G01N 27/622; H01J 49/061; H01J 49/10; H01J 49/18
See application file for complete search history.

(56) References Cited

U.S. PATENT DOCUMENTS 4,260,884 A * 4/1981 Lovelock ................ H01T 19/00
250/324
5,925,269 A * 7/1999 Bloemen .............. B23K 26/361
219/121.64

(Continued)

FOREIGN PATENT DOCUMENTS

CN       101442870 A       5/2009
CN       102479659 A  *    5/2012
(Continued)

OTHER PUBLICATIONS

"International Application No. PCT/CN2016/094164, International Search Report dated Nov. 9, 2016", w/English Translation, (Nov. 9, 2016), 6 pgs.

(Continued)

*Primary Examiner* — David E Smith
(74) *Attorney, Agent, or Firm* — Schwegman Lundberg & Woessner, P.A.

(57) ABSTRACT

The present disclosure discloses a corona discharge assembly, an ion mobility spectrometer and a corona discharge method. The corona discharge assembly includes at least one corona discharge unit, wherein, the corona discharge unit includes a pair of corona metal wires arranged in parallel, and pulses having the same amplitude but opposite polarities are applied to the corona metal wires arranged in parallel, respectively. The present disclosure can generate more reac- (Continued)

tive ions than corona needles or tips, facilitate improving sensitivity of the ion mobility spectrometer, and effectively prolong service life of a corona source to 3-10 years.

11 Claims, 3 Drawing Sheets

(51) Int. Cl.
*H01J 49/06* (2006.01)
*H01J 49/18* (2006.01)

(56) References Cited

U.S. PATENT DOCUMENTS

| | | | | |
|---|---|---|---|---|
| 2005/0116166 | A1* | 6/2005 | Krichtafovitch | H01T 19/00 250/324 |
| 2009/0135537 | A1* | 5/2009 | Yasuoka | H01T 23/00 361/213 |
| 2010/0230588 | A1* | 9/2010 | Atkinson | G01N 27/624 250/283 |
| 2010/0276587 | A1* | 11/2010 | Clark | H01J 49/0095 250/285 |
| 2014/0264021 | A1* | 9/2014 | Atamanchuk | G01N 27/622 250/336.1 |
| 2014/0299758 | A1* | 10/2014 | Chen | G01N 27/68 250/281 |

FOREIGN PATENT DOCUMENTS

| | | |
|---|---|---|
| CN | 105655228 A | 6/2016 |
| CN | 205428870 U | 8/2016 |
| JP | 59189649 U | 12/1984 |
| JP | 10255954 A | 9/1998 |

OTHER PUBLICATIONS

"International Application No. PCT/CN2016/094164, Written Opinion dated Nov. 9, 2016", (Nov. 9, 2016), 4 pgs.

"Japanese Application Serial No. 2017-563514, Office Action dated Nov. 27, 2018", w/ English Translation, (Nov. 27, 2018), 14 pgs.

* cited by examiner

US 10,317,365 B2

CORONA DISCHARGE ASSEMBLY, ION MOBILITY SPECTROMETER AND CORONA DISCHARGE METHOD

CROSS-REFERENCE TO RELATED APPLICATION

The present application is the U.S. national phase entry of PCT/CN2016/094164, with an international filing date of Aug. 9, 2016, which claims the benefit of Chinese Patent Application No. 201511032539.6, filed on Dec. 31, 2015, the entire disclosures of which are incorporated herein by reference.

TECHNICAL FIELD

The present disclosure relates to the field of security detection technology, and particularly to a corona discharge assembly, an ion mobility spectrometer and a corona discharge method.

BACKGROUND

At present, ion mobility products, as an instrument for rapid detection of explosives and drugs, has been widely used in safety inspection fields in airport, subway and venue. Most of conventional ion mobility products use radioactive sources to generate reactive ions, but the radioactive sources has high risk and is strictly controlled, and thus cannot be used for safety inspection at places such as inside the aircraft. Accordingly, many companies began to do non-radioactive source product-based research since 90s of the last century. Currently, the market mainly focuses on several non-radioactive source technologies including corona discharge, photo-ionization source, electro-spray ionization source, glow discharge and the like, and, the corona discharge and photo-ionization source are main manners of ionization source adopted by most companies.

Reactive ions generated in the corona discharge are highly various in species and are closest to those generated in radioactive sources, so the corona discharge, among all these ionization sources, is the best choice as a substitute for the radioactive source. The corona discharge source has the disadvantages of fast loss and short in life, and thus is required to be frequently replaced, increasing degree of difficulty of the instrument design.

In the prior art, there is disclosed a needle-paired positive and negative pulse corona discharge source, and it has the advantages of being able to generate both positive and negative ions, and control the reaction process between sample molecules and reactive ions by controlling a time interval between an ion gate opening signal and a pulse corona. The use of pulse effectively prolongs the needle's life, but it is still inevitable that a tip of the needle will loss. Its disadvantage is that the needle has a short life and thus needs to be replaced periodically.

There is also disclosed a direct current switching corona source. When it is switched to high voltage, reactive ions generated at a corona metal wire can make the doped molecules to be charged, while when it is switched to low voltage, the reactive ions cannot make the doped molecules to be charged. The purpose of using this is to achieve a controllable doped condition. Photo-ionization has a simple principle and is easy to realize, but its disadvantage is that the life is short. The higher the corona voltage is, the faster the needle tip losses. The more active the background gas is, the more serious pollution of the needle is.

Although frequency of usage of the high voltage is reduced by adopting the voltage switching method (i.e., a corona high-voltage is switched on to perform a corona discharge when operated while the corona high-voltage is switched to a lower level so that no corona discharge will be performed when not operated), the life of the corona source is still low.

SUMMARY

In one aspect, the present disclosure provides a corona discharge assembly comprising at least one corona discharge unit, wherein, the corona discharge unit comprises a pair of corona metal wires arranged in parallel, and pulses having the same amplitude but opposite polarities are applied to the corona metal wires arranged in parallel, respectively.

In one embodiment, the corona metal wires have a diameter ranged from 10 micrometers to 50 micrometers.

In one embodiment, the corona metal wires are made of platinum or palladium.

In one embodiment, an amplitude of the pulse is ranged from 1 kV to 5 kV.

In one embodiment, a width of the pulse is less than 1 microsecond.

In one embodiment, the at least one corona discharge unit comprises a plurality of corona discharge units; corona metal wires of the plurality of corona discharge units are arranged alternately in accordance with the polarities of the pulses applied.

In one embodiment, the corona metal wires of the corona discharge units are arranged linearly.

In one embodiment, the corona metal wires of the corona discharge units are arranged in a zigzag array manner.

In one embodiment, the corona metal wires of the corona discharge units are arranged in a ring array manner.

In another aspect, the present disclosure provides an ion mobility spectrometer comprising an ionization area, an ion gate, a drift tube and a Faraday disc arranged in sequence, wherein the abovementioned corona discharge assembly is fixed in the ionization area.

In one embodiment, an electric potential of the ionization area is equal to a direct current offset of the corona metal wires.

In one embodiment, a direction of the corona metal wire is perpendicular to an axial direction of an ion drift tube.

In still another aspect, the present disclosure also provides a corona discharge method being implemented on the abovementioned corona discharge assembly and comprising the following steps of:

applying pulses having the same amplitude but opposite polarities onto the corona metal wires.

In one embodiment, the corona discharge method further comprises a step of electrically energizing the corona metal wires to remove an oxide layer.

DETAILED DESCRIPTION OF THE EMBODIMENTS

These embodiments of the present disclosure will be described hereinafter clearly and completely with reference to the attached drawings. Obviously, the embodiments illustrated in these drawings are used to explain and illustrate the present disclosure, but not to limit the present disclosure.

Figure 1:
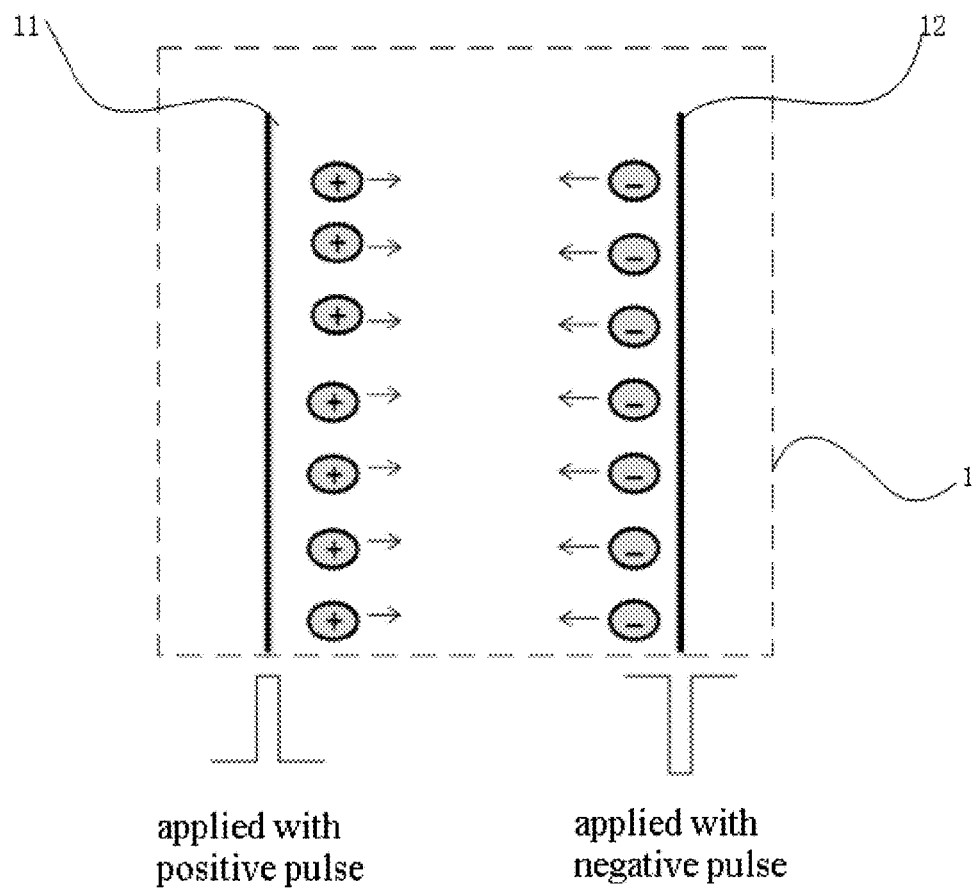
FIG. 1 is a schematic view of a structure of a corona discharge unit according to an embodiment of the present disclosure.

Referring to FIG. 1, the present disclosure provides a corona discharge assembly which is used in a corona source. The corona discharge assembly comprises at least one corona discharge unit 1, the corona discharge unit 1 comprises a pair of corona metal wires 11, 12 arranged in parallel, and pulses having the same amplitude but opposite polarities are applied respectively to the corona metal wires 11, 12 arranged in parallel. Explanations and illustrations on the corona discharge assembly according to the present disclosure will be provided in detail hereinafter.

As shown in FIG. 1, according to the present disclosure, each corona discharge unit 1 comprises a pair of corona metal wires 11, 12 arranged in parallel. The corona metal wires 11 and 12 are preferably made of platinum or palladium, or the like. It should be understood that the present disclosure is not limited to this, and other high conductivity metals having high chemical inertia, high ductility and high strength may be used to realize the present disclosure. The corona metal wires 11 and 12 may have a diameter ranged from 10 micrometers to 50 micrometers. If a diameter of the corona metal wire is too small, it will have an increased manufacturing difficulty and a high manufacturing cost; and, if the diameter of the corona metal wire is too big, its required amplitude of the pulse is too high, which make an excessive requirement on commercial pulse source.

Working process of the corona discharge assembly according to the present disclosure will be presented as follows. When the corona metal wires 11, 12 of the corona discharge unit do not work, no pulse is applied cross the corona metal wires 11, 12, and, the corona metal wire 11 and the corona metal wire 12 are in a zero electric field region and are under equal potential. When the corona metal wires 11, 12 of the corona discharge unit work, pulses having the same amplitude but opposite polarities are applied on the corona metal wires 11, 12 of the corona discharge unit, respectively. For example, a pulse having positive polarity (+) is applied on the corona metal wire 11 while a pulse having negative polarity (−) is applied on the corona metal wire 12. Amplitudes of the pulses applied on the corona metal wire 11 and the corona metal wire 12 are preferably ranged from 1 kV to 5 kV. In this case, positive pulse corona discharge is performed at the corona metal wire 11 while negative pulse corona discharge is performed at the corona metal wire 12. Positive ions are produced at the corona metal wire 11 while negative ions are produced at the corona metal wire 12. Positive ions produced at the corona metal wire 11 move towards the corona metal wire 12 under a strong electric field created from the pulses applied on the corona metal wire 11 and the corona metal wire 12. Negative ions produced at the corona metal wire 12 move towards the corona metal wire 11 under a strong electric field created from the pulses applied on the corona metal wire 11 and the corona metal wire 12. Width of the pulse applied on the corona metal wire 11 and the corona metal wire 12 is preferably less than 1 microsecond. The width of the pulse applied on the corona metal wire 11 and the corona metal wire 12 to implement an effective discharge is short, accordingly, when the corona discharge is performed, positive ions are produced at the corona metal wire 11 but the time is not long enough for the positive ions to arrive at the corona metal wire 12 while negative ions are produced at the corona metal wire 12 but the time is not long enough for the negative ions to arrive at the corona metal wire 11. After completion of the pulses, the positive ions produced at the corona metal wire 11 and the negative ions produced at the corona metal wire 12 spread and react with molecules ($O_2$, $H_2O$, $N_2$) in the air, in field-free space, to generate plenty of reactive ions ($O_2^-$, $(H_2O)H^+$, $NO^+$ and their hydrates). After sufficient charge exchange between the sample molecules M and the reactive ions in the ionization area, the produced sample ions ($M(H_2O)_nO_2^-$, $M(H_2O)_n H^+$ and the like, n=1, 2, 3, . . . ) come into the drift tube, and then arrive at the Faraday disc under the action of a drift field, to achieve the object of identifying substance in accordance with different flight times.

Figure 2:
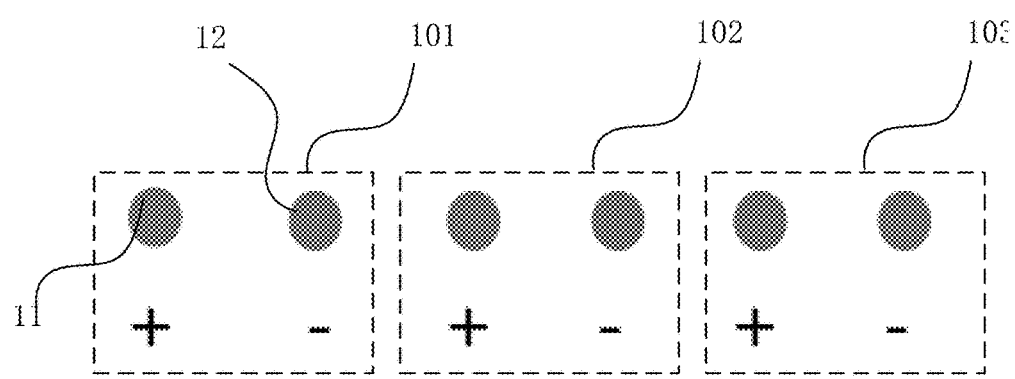
FIG. 2 is a schematic sectional view of a structure of a plurality of corona discharge units where corona metal wires are horizontally arranged according to an embodiment of the present disclosure.
Figure 3:
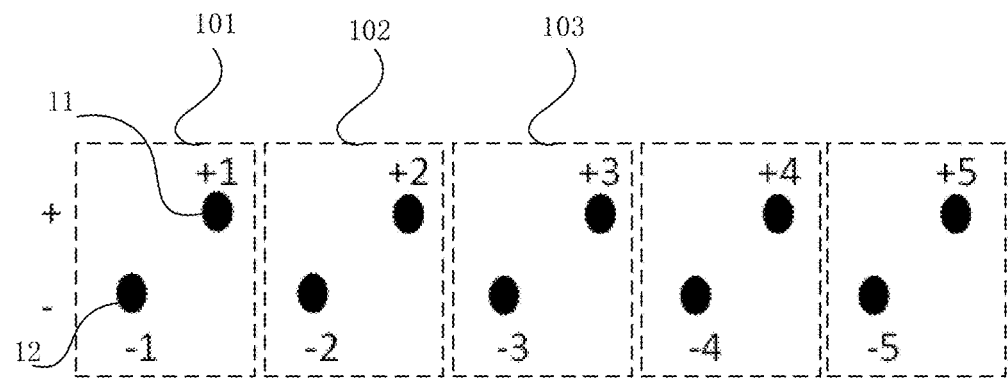
FIG. 3 is a schematic sectional view of a structure of a plurality of corona discharge units where corona metal wires are arranged in two layers according to an embodiment of the present disclosure.
Figure 4:
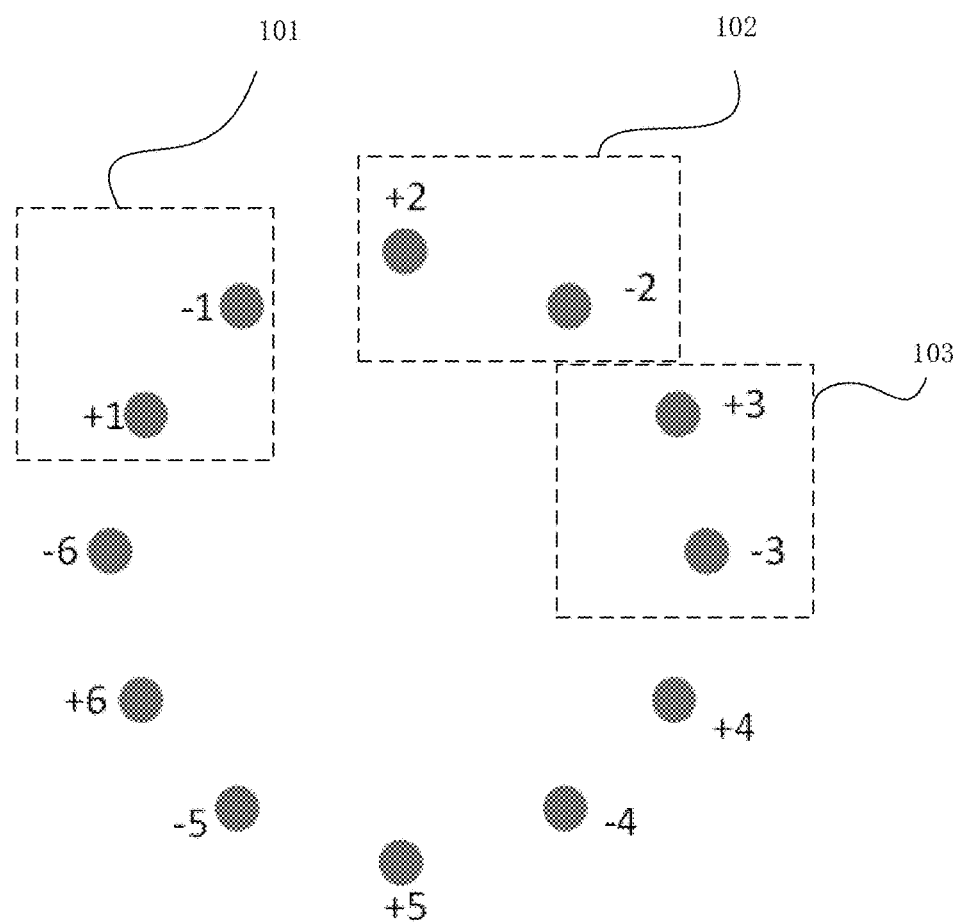
FIG. 4 is a schematic sectional view of a structure of a plurality of corona discharge units where corona metal wires are arranged in a ring according to an embodiment of the present disclosure.

In this present disclosure, corona metal wires 11, 12 are adopted in the corona discharge assembly, to effectively prolong service life of the corona source. Nevertheless, the corona metal wires 11, 12 also will be consumed accordingly in use. Referring to FIG. 2 to FIG. 4, in order to prolong service life of the corona source as far as possible, a plurality of corona discharge units 1 are adopted in the corona source, and the corona metal wires in the plurality of corona discharge units 1 are arranged alternately in accordance with the polarities of the pulses applied. As shown in FIG. 2 to FIG. 4, the corona discharge assembly comprises a plurality of corona discharge units 1. The corona metal wires 11, 12 of the corona discharge units 1 are arranged in parallel, while positive and negative corona metal wires 11, 12 are arranged alternately. In these Figures, + represents positive corona metal wire while—represents negative corona metal wire. Referring to FIG. 2 to FIG. 4, in the present disclosure, the plurality of corona discharge units 1 adopted in the corona source may be operated alternately or simultaneously. Manners of operating the plurality of corona discharge units 1 adopted in the corona source will be respectively described in detail hereinafter.

A manner is that the plurality of corona discharge units 101, 102, 103 adopted in the corona source are operated alternately, only some of the corona discharge units are operated (i.e., one corona discharge unit or two corona discharge units are operated) at each time. Specifically, as shown in FIG. 2 to FIG. 4, in operation, pulses are applied to only the corona metal wire 11 (−1) and the corona metal wire 12 (+1) of the first corona discharge unit 101, while the corona metal wires of the rest corona discharge units 102, 103 are still in original isopotential. After a period of time (months) of operation, when the corona metal wires "−1", "+1" do not perform corona discharge anymore, it is switched through a circuit to operate the second corona discharge unit 102, and pulses are applied to only the corona metal wire 11 (−2) and the corona metal wire 12 (+2) of the second corona discharge unit 102. After that, similarly, it is switched to operate the third corona discharge unit 103. As a result, service life of the corona source is effectively prolonged.

Another manner is that the plurality of corona discharge units 101, 102, 103 adopted in the corona source are operated simultaneously, referring to FIG. 2 to FIG. 4, all the positive corona metal wires 11 of the plurality of corona discharge units 101, 102, 103 are electrically connected, and all the negative corona metal wires 12 are electrically connected, however, corona discharge is performed only between one or several pairs of corona metal wires which have closest spacing(s) therebetween, while no corona discharge is performed between the rest of these corona metal wires. The manner of operating the plurality of corona discharge units simultaneously has the following advantages: (1) when one pair of corona metal wires or some corona metal wires do not operate, the rest of these corona metal wires begin to perform corona discharge, which effectively prolongs service life of the corona source; and, (2) corona discharge performed by multiple-corona metal wire structure will generate much more ions, thereby effectively increasing quantity of the reactive ions.

Referring to FIG. 2, in one implementation of the present disclosure, a plurality of corona metal wires 11, 12 of a plurality of corona discharge units 101, 102, 103 adopted in the corona source are arranged linearly. These corona metal wires 11, 12 are arranged in a line in the manner of +, −, +, −, +, −. Corona discharges are performed between adjacent corona metal wires 11, 12, while corona discharges are performed alternately between adjacent corona discharge units.

Referring to FIG. 3, in another implementation of the present disclosure, a plurality of corona metal wires of a plurality of corona discharge units 101, 102, 103 adopted in the corona source are arranged in a zigzag array manner. That is, the plurality of corona metal wires are arranged wavily. Two rows of the corona metal wires 11, 12 constitute positive and negative corona sources, in which an upper row of corona metal wires are positive corona metal wires 11 while a lower row of corona metal wires are negative corona metal wires 12. For example, when all of the positive corona metal wires 11 and the negative corona metal wires 12 operate, corona discharges are performed between adjacent corona metal wires 11, 12 ("+1" and "−1", "−2"). Corona discharges are performed alternately between the upper and lower rows of corona metal wires 11, 12, while corona discharges are performed alternately between adjacent corona discharge units.

Referring to FIG. 4, in yet another implementation of the present disclosure, cross sections of the corona metal wires 11, 12 of a plurality of corona discharge units 101, 102, 103 adopted in the corona source are arranged in a ring array. All the corona metal wires 11, 12, regarded as a whole, preferably form a circle, in which positive pulse is applied to a corona metal wire "+1" while negative pulse is applied to a corona metal wire "−1" and/or a corona metal wire "−6", so that positive and negative corona discharges are performed. Corona discharges are performed alternately among the corona metal wires 11, 12 arranged in a ring array, while corona discharges are performed alternately between adjacent corona discharge units.

It should be understood that, in the corona source shown in FIG. 2 to FIG. 4 of the present disclosure, the plurality of corona discharge units may be operated alternately or simultaneously, and specific processes of the operation can refer to the above implementations and will be omitted for clarity.

Figure 5:
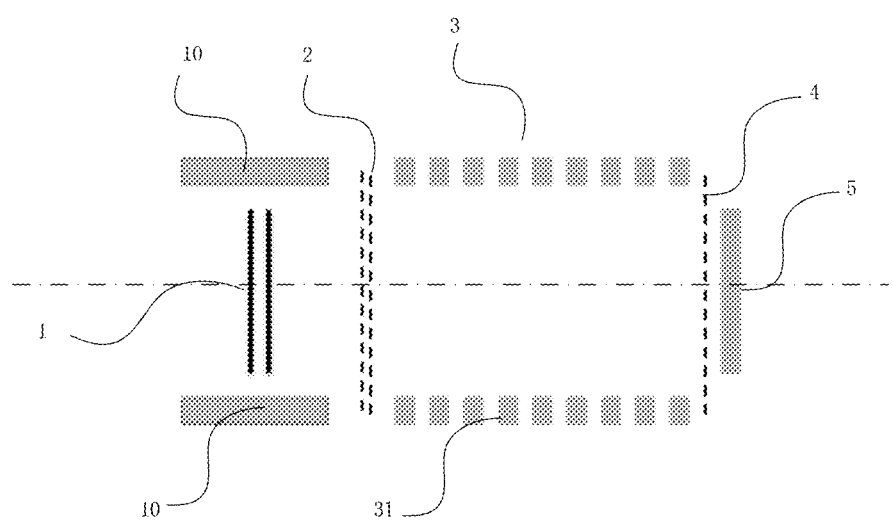
FIG. 5 is a schematic view of a structure of an ion mobility spectrometer according to an embodiment of the present disclosure.

In order to further present advantage of the corona discharge assembly according to the present disclosure, the present disclosure also provides an ion mobility spectrometer with the abovementioned corona discharge assembly. Referring to FIG. 5, the ion mobility spectrometer comprises an ionization area 10, an ion gate 2, a drift tube (migration area) 3 and a Faraday disc 5 arranged in sequence, a corona discharge assembly 1 is fixed in the ionization area and is the one described in the above. The ion mobility spectrometer according to the present disclosure will be described in detail hereinafter.

Referring to FIG. 5, the corona source in the ionization area comprises one corona discharge assembly 1, and corona metal wires of the corona discharge assembly 1 are fixed within the ionization area 10, and directions of the corona metal wires preferably are perpendicular to a direction of ion drift. An electric potential of the ionization area 10 is equal to a direct current offset of the corona metal wires. In the present disclosure, the ion gate 2 may be a BN gate or a Tnydal gate (, it should be noted that the present disclosure is not limited to this, and any type of the gate existing in prior art can be used in the present disclosure). The drift tube 3 is formed by a series of electrodes 31. An aperture grid 4 is disposed between the drift tube 3 and the Faraday disc 5.

Referring to FIG. 5, operational process of the ion mobility spectrometer including the corona discharge assembly according to the present disclosure is described as follows. Pulses having the same amplitude but opposite polarities are respectively applied onto two corona metal wires in the ionization area 10, to produce plenty of positive and negative ions between surfaces of the two corona metal wires. These positive and negative ions move towards opposite corona metal wires. Due to the short width of pulse applied, the pulse ends before plenty of positive and negative ions arrive at opposite corona metal wires and the positive and negative ions spread and react with molecules in the air within the ionization area 10 to generate plenty of reactive ions. After sufficient charge exchange between the sample molecules and the reactive ions in the ionization area 1, the sample ions are produced. After the ion gate 2 opens, the sample ions come into the drift tube 3, and then arrive at the Faraday disc 5 through the aperture grid 4 under the action of an electric field. The corona metal wires can generate more reactive ions than corona needles or tips, facilitating improving sensitivity of the ion mobility spectrometer. When the corona metal wire is covered with an oxide layer by contamination of impurities and samples, the oxide layer may be eliminated through electrifying the corona metal wire to prolong service life of the corona metal wire.

In order to further present advantage of the corona discharge assembly according to the present disclosure, the present disclosure also provides a corona discharge method being implemented on the abovementioned corona discharge assembly. This method comprises the following steps of: applying pulses having the same amplitude but opposite polarities onto the corona metal wires. When the corona metal wire is covered with an oxide layer by contamination of impurities and samples (mainly a variety of organic matters), the oxide layer may be eliminated through electrifying the corona metal wire. When the corona metal wire is electrified and thus heated, these matters will be eliminated by volatilization or oxidation, prolong service life of the corona metal wire.

Concerning the above, the corona discharge assembly, the ion mobility spectrometer and the corona discharge method according to the present disclosure can generate more reactive ions than corona needles or tips, facilitate improving sensitivity of the ion mobility spectrometer, and effectively prolong service life of a corona source to 3-10 years.

The above embodiments merely intend to exemplarily illustrate the present invention, but not to limit the present invention. It would be appreciated by those skilled in the art that various changes or modifications may be made in these embodiments without departing from the principles and spirit of the present invention, the scope of which is defined in the claims and their equivalents.

What is claimed is:

1. A corona discharge assembly comprising a plurality of corona discharge units, wherein, each of the corona discharge unit comprises a pair of corona metal wires arranged in parallel, pulses having the same amplitude but opposite polarities are respectively applied to the corona metal wires arranged in parallel, corona metal wires of the plurality of corona discharge units are arranged alternately in accordance with the polarities of the pulses applied, and the corona metal wires of the corona discharge units are arranged in a zigzag array manner or in a ring array.

2. The corona discharge assembly of claim 1, wherein, the corona metal wires have a diameter ranged from 10 micrometers to 50 micrometers.

3. The corona discharge assembly of claim 1, wherein, the corona metal wires are made of platinum or palladium.

4. The corona discharge assembly of claim 1, wherein, an amplitude of the pulses is ranged from 1 kV to 5 kV.

5. The corona discharge assembly of claim 1, wherein, a width of the pulses is less than 1 microsecond.

6. The corona discharge assembly of claim 1, wherein, e corona metal wires of the corona discharge units are arranged linearly.

7. An ion mobility spectrometer comprising an ionization area, an ion gate, a drift tube and a Faraday disc arranged in sequence, a corona discharge assembly of claim 1 being fixed in the ionization area.

8. The ion mobility spectrometer of claim 7, wherein, an electric potential of the ionization area where the corona metal wires are fixed within is equal to a direct current offset of the corona metal wires.

9. The ion mobility spectrometer of claim 7, wherein, a direction of the corona metal wire is perpendicular to an axial direction of an ion drift tube.

10. A corona discharge method being implemented on a corona discharge assembly of claim 1 and comprising the following steps of:

applying pulses having the same amplitude but opposite polarities onto the corona metal wires.

11. The corona discharge method of claim 10 further comprising a step of electrically energizing the corona metal wires to remove an oxide layer.

* * * * *